United States Patent
Garcia et al.

(10) Patent No.: US 6,225,053 B1
(45) Date of Patent: *May 1, 2001

(54) DETECTION OF HEPATITIS B VIRUS

(75) Inventors: Mariana Garcia, Arlington, VA (US); Ming Chan, Ft. Myers, FL (US); Attila Lörincz, North Potomac, MD (US)

(73) Assignee: Digene Corporation, Gaithersburg, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/989,865

(22) Filed: Dec. 12, 1997

(51) Int. Cl.$^7$ .............................. C12Q 1/68; G01N 33/53; C12N 7/00; C07H 21/04

(52) U.S. Cl. .................................. 435/6; 435/6; 435/7.1; 435/235.1; 536/24.3; 536/24.31; 536/24.32

(58) Field of Search .......................... 435/6, 7.1, 235.1; 536/24.3, 24.31, 24.32

(56) References Cited

U.S. PATENT DOCUMENTS

| | | | |
|---|---|---|---|
| H1431 | * 4/1995 | Kern et al. ............................... | 435/6 |
| 4,429,646 | * 2/1984 | McAleer et al. ........................ | 424/89 |
| 4,562,159 | * 12/1985 | Shafritz et al. ....................... | 436/501 |
| 4,563,417 | 1/1986 | Albarella et al. . | |
| 4,683,195 | 7/1987 | Mullis et al. . | |
| 4,683,202 | 7/1987 | Mullis . | |
| 4,732,847 | 3/1988 | Stuart et al. . | |
| 4,743,535 | 5/1988 | Carrico . | |
| 4,833,084 | 5/1989 | Carrico . | |

FOREIGN PATENT DOCUMENTS

| | | |
|---|---|---|
| 0 186 526 | 7/1986 | (EP) . |
| 0 640 399 | 3/1995 | (EP) . |
| WO 93/10263 | * 5/1993 | (WO) . |

OTHER PUBLICATIONS

Cooper T. The Tools of Biochemistry, John Wiley 7 Sons, pp.309,322–326, 1977.*

Chervenka C.H. A Manual of Methods for the analytical ultracentrifuge pp23–33, 1969.*

Hoofnagle et al., "α–Interferon therapy of chronic hepatitis B. Current Status and Recommendations," *J. Hepatol.* 11(1):S100–S107 (1990).

Ishikawa et al., "Enzyme–Labeling of Antibodies and Their Fragments for Enzyme Immunoassay and Immonohistochemical Staining," *J. Immunoassay* 4(1):209–237 (1983).

Kitawaga, Y. and Stollar, B.D., "Comparison of Poly(A)–Poly(dT) and Poly(I)–Poly(dC) as Immunogens for the Induction of Antibodies to RNA–DNA Hybrids," *Mol. Immunology* 19(3):413–420 (1982).

Kramer, F.R. and Lizardi, P.M., "Replicatable RNA reporters", *Nature* 339:401–402 (1989).

Kwoh, D.Y., et al., "Transcription–based amplification system and detection of amplified human immunodeficiency virus type 1 with a bead–based sandwich hybridization format," *Proc. Natl. Acad. Sci. USA* 86(3):1173–1177 (1989).

Landegren, U., et al., "A Ligase–Mediated Gene Detection Technique," *Science* 241:1077–1080 (1988).

Landegren, U., et al., "DNA Diagnostics—Molecular Techniques and Automations," *Science* 242:229–237 (1988).

Lizardi., et al., "Exponential amplification of recombinant–RNA hybridization probes", *Bio/Technology* 6:1197–1202 (1988).

Loh, E.Y., et al., "Polymearase Chain Reactions with Single–Sided Specificity: Analysis to T Cell Receptor δ Chain," *Science* 243:217–220 (1989).

Lomeli, H., et al., "Quantitative assays based on the use of replicatable hybridization probes", *Clin. Chem.* 35(9):1826–1831 (1989).

Marz, J.L., "Multiplying Genes by Leaps and Bounds," *Science* 240:1408–1410 (1988).

Means, G. and Feeney, R., "Chemical Modifications of Proteins: History and Applications," *Bioconj. Chem.* 1:2–12 (1990).

PCR Protocols A Guide to Methods and Applications by Michael A. Innis, David H. Gelfand, John J. Sninsky and Thomas J. White, pp. 39–45 and 337–385 (Academic Press, Inc., Harcourt Brace Jovanovich, Publishers, 1990).

Southern, "Detection of Specific Sequences among DNA Fragments Separated by Gel Electrophoresis," *J. Mol. Biol.* 98:503–517 (1975).

Stoflet, E.S., et al., Genomic Amplification with Transcript Sequencing, *Science* 239:491–494 (1988).

Stuart et al., "Location of the 18/28S ribosomal RNA genes in two Hawaiian *Drosophila* species by monoclonal immunological identification by RNA–DNA hybrids in situ," *Proc. Natl. Acad. Sci., USA* 78(6):3751–3754 (1981).

Wu, D.Y. and Wallace, R.B., "The Ligation Amplification Reaction (LAR)—Amplification of Specific DNA Sequences Using Sequential Rounds of Template–Dependent Ligation," *Genomics* 4:560–569 (1989).

Ansari, et al., "ELISA Solid Phase: Stability and Binding Characteristics," *J. Immunol. Methods* 84:117–124 (1985).

Barringer, J.J., et al., Blunt–end and single–strand ligations by *Escherichia coli* ligase: influence on an in vitro amplification, *Gene* 89:117–122 (1990).

(List continued on next page.)

*Primary Examiner*—Kenneth R. Horlick
*Assistant Examiner*—Jeffrey Siew
(74) *Attorney, Agent, or Firm*—Arnall Golden & Gregory, LLP

(57) ABSTRACT

An improved assay disclosed for detecting viral nucleic acid sequences. The improvement involves concentration viral particles from a biological sample by centrifugation. Once concentrated, the nucleic acid molecules in the viral particles can be manipulated or detected using any suitable procedure. Many such procedure are know and can be used with the concentrated viral nucleic acid molecules. Preferably, the concentrated viral nucleic acid is detected using a detection assay.

12 Claims, No Drawings

OTHER PUBLICATIONS

Boguslawski et al., "Characterization of monoclonal antibody to DNA—RNA and its application to immunodetection of hybrids," *J. Immunol. Methods* 89:123–130 (1986).

Chu, B.C.F., et al., "Synthesis of an amplifiable reporter RNA for bioassays," *Nucl. Acids Res.* 14(14):5591–5603 (1986).

Compton, J., "Nucleic acid sequence–based amplification," *Nature* 350(6313):91–92 (1991).

Cooper, *The Tools of Biochemistry*, (1977) (Table of Contents).

Coutlee, et al., "Comparison of Colorimetric, Flourescent, and Enzymatic Amplification Substrate Systems in an Enzyme Immunoassay for Detection of DNA–RNA Hybrids," *J. Clin. Microbiol.* 27(5):1002–1007 (1989).

Fleminger, G., et al., "Oriented Immobilization of Periodate–Oxidized Monoclonal Antibodies on Amino and Hydrazide Derivatives of Eupergit C," *Appl. Biochem. Biotech.* 23(1):123–137 (1990).

Grunstein et al., "Colony hybridization: A method for the isolation of cloned DNAs that contain a specific gene," *Proc. Natl. Acad. Sci. USA* 72(10):3961–3965 (1975).

Haase, A.T., et al., "Amplification and detection of lentiviral DNA inside cells", *Proc. Natl. Acad. Sci. (USA)* 87(13):4971–4975 (Jul. 1990).

Haun, M. and Wasi, S., "Biotinylated Antibodies Bound to Streptavidin Beads: A Versatile Solid Matrix for Immunoassays," *Anal. Biochem.* 191:337–342 (1990).

* cited by examiner

DETECTION OF HEPATITIS B VIRUS

BACKGROUND OF THE INVENTION

The present invention relates to the field of detection assays of viruses in general and more particularly relates to improved detection of hepatitis B virus.

Hepatitis B virus (HBV), formerly termed serum hepatitis, is a member of a group of small DNA-containing viruses that cause persistent noncytopathic infections of the liver, is an infectious agent of humans that is found worldwide and which is perpetuated among humans in a large reservoir of chronic carriers. It is estimated that about 6 to 7% of the earth's population is infected (300 million carriers). HBV infection in humans can cause severe jaundice, liver degeneration and death. HBV enters predominantly by the parenteral route, has a characteristic incubation period of 60 to 160 days, and may persist in the blood for years in chronic carriers. The prevalence of the infection is not uniform throughout the world. There is a geographic gradient in distribution of HBV. It is lowest in North America and Western Europe, where the virus can be detected in 0.1 to 0.5% of the population, and highest in Southeast Asia and sub-Saharan Africa, where the frequency of infection may vary from 5 to 20% of the population. This skewed distribution parallels that of hepatocellular carcinoma and provides strong epidemiologic evidence for an association between chronic HBV infection and this type of malignancy.

Hepatitis B is of great medical importance because it is probably the most common cause of chronic liver disease, including hepatocellular carcinoma in humans. Infected hepatocytes continually secrete viral particles that accumulate to high levels in the blood. These particles are of two types: (i) noninfectious particles consisting of 22 nm spheres and filaments of excess viral coat protein (HBsAg) and containing no nucleic acid (in concentrations of up to $10^{13}$ particles/ml blood) which are referred to as the Australian antigen (AU), and (ii) infectious, DNA-containing particles (Dane particle nucleocapsids) consisting of a 28 nm nucleocapsid core (HBcAg) around which is assembled an envelope containing the major viral coat protein, carbohydrate, and lipid, present in lower concentrations ($10^9$ particles/ml blood). The human hepatitis B virus is a member of the Hepadna Viridae family, with close relatives including woodchuck hepatitis virus (WHV), duck hepatitis virus (DHV), and ground squirrel hepatitis virus (GHV) (Robinson, 1990). Like retroviruses, the hepadnavirus utilizes reverse transcription of its 3.2 Kb DNA genome (Pugh, 1990). The genome of hepatitis B virus is circular and partially single-stranded, containing an incomplete plus strand. The incomplete plus strand is complexed with a DNA polymerase in the virion which has been shown to elongate the plus strand using the complete minus strand as the template. These morphological and structural features distinguish hepatitis B viruses from all known classes of DNA-containing viruses.

The replication cycle of hepatitis B viruses is also strikingly different from other DNA-containing viruses and suggests a close relationship with the RNA-containing retroviruses. The principal unusual feature is the use of an RNA copy of the genome as an intermediate in the replication of the DNA genome. Infecting DNA genomes are converted to a double-stranded form which serves as a template for transcription of RNA. Multiple RNA transcripts are synthesized from each infecting genome, which either have messenger function or DNA replicative function. The latter, termed "pre-genomes," are precursors of the progeny DNA genomes because they are assembled into nucleocapsid cores and reverse-transcribed into DNA before coating and export from the cell. Thus each mature virion contains a DNA copy of the RNA pre-genome and a DNA polymerase.

The first DNA to be synthesized is of minus strand polarity and is initiated at a unique site on the viral genetic map. Very small nascent DNA minus strands (less than 30 nucleotides) are covalently linked to a protein, and are likely to act as primer for minus strand DNA synthesis. Growth of the minus strand DNA is accompanied by a coordinate degradation of the pre-genome so that the product is a full-length single-stranded DNA, rather than an RNA:DNA hybrid. Plus strand DNA synthesis has been observed only after completion of the minus strand, and initiates at a unique site close to the 5' end of the minus strand. Complete elongation of the plus strand is not a requirement for coating and export of the nucleocapsid cores, thus most extracellular virions contain incomplete plus strands and a large single-stranded gap in their genomes. Because the hepatitis virus genome is autonomous and does not utilize a DNA-to-DNA pathway for its replication, continuous intracellular replication of its genome is essential for the maintenance of the virus.

HBV is detected by immunologic techniques such as immune electron microscopy, complement-fixation, immune adherence, enzyme-linked immunosorbent assay (ELISA) or radioimmunoassay (RIA). All blood for transfusion must be screened for HBV to prevent transmission of the virus to blood recipients. Early detection of HBV in infected patients is also important because exposure to blood or objects potentially contaminated with blood or even body excretions may cause infection.

Conventional HBV DNA assays test for the presence of hepatitis B virus genomic DNA in human serum using a full genomic (3.2 Kb) RNA probe. For HBV DNA testing a quantitative assay would be particularly advantageous because the level of HBV DNA in serum correlates with severity of liver disease. A quantitative HBV DNA test would be useful for monitoring chronic carriers of HBV. For example, the effectiveness of antiviral therapy such as that described by Hoofnagle et al., *J. Hepatol*. 11S:100 (1990), can be assessed more easily with an improved detection assay.

In summary, there is a need for a hybridization assay for clinical diagnosis and quantitative analysis of viral infections, especially HBV, and genetic mutational defects, that is economically feasible for screening large numbers of samples with great sensitivity.

It is therefore an object of the present invention to provide a cost-effective, sensitive, assay for the detection of viral nucleic acids in a sample.

It is a further object of the present invention to provide a cost-effective, sensitive, assay for the quantitation of nucleic acids in a sample.

It is a further object of the present invention to provide an assay in which sample preparation is simple and rapid.

It is a further object of the present invention to provide an assay in which sample preparation does not involve extractions, or other time-consuming purification methods.

It is a further object of the present invention to provide an assay having minimal false positives.

It is a further object of the present invention to provide an accurately quantitative test for monitoring the level of virus in a viral infection.

It is a further object of the present invention to provide a sample for an assay that allows for an assay with a lower detection limit.

It is a further object of the present invention to provide a kit that can be used to screen large numbers of samples for microbial and viral infections.

SUMMARY OF THE INVENTION

An improved assay is disclosed for detecting viral nucleic acid sequences. The improvement involves concentrating viral particles from a biological sample by centrifugation. Once concentrated, the nucleic acid molecules in the viral particles can be manipulated or detected using any suitable procedure. Many such procedures are known and can be used with the concentrated viral nucleic acid molecules. Preferably, the concentrated viral nucleic acid is detected using a detection assay. A preferred form of the disclosed assay is performed generally as follows. A test sample of blood is collected with a chemically inert device and serum is separated. The serum is subjected to a centrifugation step which concentrates the viral particles. This step has a significant effect on the accuracy and sensitivity of the subsequent detection assay. The reconstituted, concentrated sample is then treated with a base. The treated sample is incubated with nucleic acid probes, diluted in a neutralizing buffer, that are specific for target nucleic acid sequence, such as HBV DNA sequences, for a sufficient amount of time to allow hybridization of the sample nucleic acid sequence to the probes. The hybrids are then bound to anti-hybrid antibodies immobilized on a solid phase. Non-hybridized probe is removed, preferably by incubating the captured hybrids with an enzyme, such as RNAase, that degrades non-hybridized probe. Hybridization is detected by conventional means such as a direct labelled anti-hybrid antibody, a labelled antibody specific for an unlabelled anti-hybrid antibody, a direct labelled probe or a modified probe for which a labelled antibody is specific.

For detection of amplification reaction products, the sample is collected as described above and nucleic acid sequences are amplified by a nucleic sequence amplification method, such as the polymerase chain reaction (PCR), using a ligand-bound primer, such as a biotinylated primer. The amplification product is denatured with base and hybridized to unlabelled RNA probe in neutralizing buffer as described above. The hybrids are bound to a solid phase that has been coated with a ligand that is complementary to the ligand bound to the primer, such as avidin, and are detected by conventional means as described above.

The concentration step provides a method to concentrate HBV, or other, virions and can be used in combination with any assay to improve sensitivity.

DETAILED DESCRIPTION OF THE INVENTION

An improved assay is disclosed for detecting viral nucleic acid sequences. The improvement involves concentrating viral particles from a biological sample by centrifugation. Once concentrated, the nucleic acid molecules in the viral particles can be manipulated or detected using any suitable procedure. Many such procedures are known and can be used with the concentrated viral nucleic acid molecules. Preferably, the concentrated viral nucleic acid is detected using a detection assay. A preferred form of detection assay is a hybrid capture assay, a preferred example of which is described in WO 93/10263. This preferred form of the disclosed assay is performed generally as follows.

A sample of blood is collected and the serum is separated. The serum is subjected to a centrifugation step to concentrate the viral nucleic acid using a precipitation buffer. The sample is then subjected to alkaline pH to denature and, if necessary, nick the nucleic acids in the sample. The treated, or hydrolyzed, target nucleic acids are hybridized to a probe or group of probes diluted in a neutralizing buffer. Most preferably, the target nucleic acids are DNA and the probe is a complementary RNA sequence.

An anti-hybrid antibody, either polyclonal or monoclonal, is immobilized on a solid phase such as a test tube or polystyrene bead. It will be understood by those skilled in the art that the immobilized antibody can be bound directly to the solid phase or indirectly by use of a primary binding antibody or protein, such as streptavidin or protein G, that is bound to the solid phase and which subsequently binds the anti-hybrid antibody, a derivatized anti-hybrid antibody, a functional fragment of the anti hybrid antibody, or a derivatized functional fragment of the anti-hybrid antibody. Any solid phase such as plastic or glass microparticles, beads, dip-sticks, test tubes or microtiter plates can be used.

The hybridized sample is placed in the antibody-coated tube for a sufficient amount of time to allow binding or capture of the hybrid by the anti-hybrid antibody. An enzyme that digests single-stranded RNA or RNA-RNA hybrids, such as an RNAase is then added to the sample to eliminate any non-hybridized probe. Most preferably, the RNAase and a hybrid detection means, described below are combined as a single reagent. Alternatively, non-hybridized probe can be removed by washing the sample.

Hybridization is then detected by conventional means well known in the art such as with a direct labelled polyclonal or monoclonal antibody specific for the hybrid, a labelled antibody specific for an unlabelled anti-hybrid antibody, or the RNA probe or probes can be directly labelled, or modified and detected with a labelled antibody specific for the modified probe. Most preferably, the label is an enzyme, a fluorescent molecule or a biotin-avidin conjugate and is non-radioactive. The label can then be detected by conventional means well known in the art such as a calorimeter, a luminometer or a fluorescence detector.

A second preferred embodiment of the hybridization assay, for detection of amplified nucleic acid sequences, is performed generally as described above with the following modifications.

Primers for amplification of the nucleic acid sequences of interest contained in the sample are attached to a ligand, such as biotin. Preferably, for PCR amplification, 5'-biotinylated primers are synthesized or purchased from commercially available sources such as National Biosciences, inc. (Plymouth, Minn.).

Prior to treatment with alkaline pH as described above, nucleic acid sequences in the sample are amplified, using the ligand-bound primers, in accordance with conventional amplification methods as described in more detail below. The resulting amplification products are then subjected to alkaline pH and are hybridized to a probe or group of probes as described above.

Instead of coating the solid phase with an anti-hybrid antibody as described above, the solid phase is coated with a ligand complementary to the ligand that is attached to the primer. For example, if the primer is biotinylated, then the solid phase is coated with a complementary ligand such as streptavidin. Most preferably, streptavidin-coated microtiter plates are used. These plates may be coated passively or purchased commercially from Xenopore (Saddle Brook, N.J.) or prepared using the methods outlined below for immobilization of anti-hybrid antibody.

Sample Collection and Concentration

A blood sample is collected with a syringe, and serum is separated by conventional means. The serum sample, between about 0.5 to 1 ml, is added to about 50 µl precipitation buffer in a sample preparation centrifuge tube. The precipitation buffer is a buffered solution containing 0.44 µm polystyrene beads, 10 mM Tris·Cl and 1 mM EDTA and preferably includes color beads that allow visualization of the resulting centrifuged pellet. The tubes are mixed by inverting 5 to 6 times. The specimens and control are centrifuged at 4° C. for the time required to concentrate the target nucleic acid, as determined according to the equation described in the next section.

Immediately after centrifugation the supernatant is carefully removed, without disturbing the pellet, using a small, thin-tipped plastic transfer pipette. The supernatant is discarded into a sodium hypochloride solution. 25 to 50 µl of previously tested target nucleic acid negative serum is added to resuspend the pellet, the volume depending upon whether the sample will be further processed in a sample preparation microplate or a hybridization tube. For the tube the pellet should be reconstituted in the larger volume. The tubes are mixed on a vortex on medium setting for approximately 60 seconds or until completely dissolved. The tubes are quickly spun in a microfuge to bring all of the volume down. 30 µl of the reconstituted pellet is added to the sample preparation microplate or 50 µl to the hybridization tubes.

Calculation of Centrifugation Conditions

Sedimentation time of a molecule in a particular rotor having a radius r and rotating at an RPM can be calculated if the sedimentation coefficient for the molecule is known. See *The Tools of Biochemistry*, Cooper, (1977). The sedimentation coefficient, s, most commonly expressed as Svedberg units (S) ($10^{-13}$ seconds) can be calculated from equation 1:

$$s = \phi \frac{(\rho_p - \rho_m)}{f} \quad (1)$$

where φ is the volume of the particle in $cm^3$, $\rho_p$ is the density of the particle in $g/cm^3$, $\rho_m$ is the density of the medium in $g/cm^3$, and f is the frictional coefficient in g/sec. The frictional coefficient depends upon the size and shape of the molecule and the viscosity of the medium through which it is moving.

The sedimentation time can be calculated from equation 2:

$$T = \frac{1}{s} \frac{(\ln r_t - \ln r_o)}{\omega^2} \quad (2)$$

where $r_t$ is the radius of the rotor at the bottom of the rotor and $r_o$ is the radius at the top of the rotor, and ω is the angular velocity in radians. ω can be calculated from equation 3:

$$\omega = \frac{\pi (\text{rpm})}{30} \quad (3)$$

From these formulas and principles, the following equation 4 can be used to calculate the time needed to sediment a viral particle of interest from a biological sample.

$$T = \frac{1}{s} \frac{(\ln r_t - \ln r_o)}{(0.1047 \cdot \text{RPM})^2} \quad (4)$$

where s is the sedimentation coefficient, $r_t$ is the rotor bottom radius, $r_o$ is the rotor top radius, RPM is the revolutions per minute of the rotor, and T is the time in seconds. In general, it is preferred that the highest spin rate be used since this will minimize the time needed for centrifugation. The equation above can be adapted to any rotor by using the applicable radius values. It is preferred that the spin rate in RPM be greater than 15,000, and it is more preferred that the spin rate be greater than 20,000.

The physical characteristics of HBV, including the sedimentation coefficient of the HBV viral particle (referred to as the Dane particle nucleocapsid) are summarized in the following Table 1. The sedimentation coefficient is used with the formula above to determine the time needed for centrifugation of the biological sample.

TABLE 1

|  | AU (Australian antigen) | Dane Particles | Dane Particle Nucleocapsid |
| --- | --- | --- | --- |
| Shape | filaments | spherical and filaments | particulate |
| Size (diameter) | 22 nm | 42 nm | 28 nm |
| Length | 50–1000 nm | Various |  |
| Sedimentation coefficient | 40–54 S |  | 110 S |
| Buoyant Density in CsCl | 1.18–1.22 g/cm³ | 1.24–1.27 g/cm³ | 1.30–1.36 g/cm³ |

Using the sedimentation coefficient of 110S (that is, $110 \times 10^{-13}$) for the Dane particle nucleocapsid, and a Heraeus Contifuge 28RS with a 28RS rotor (25000–38000×g), having a bottom rotor radius of 7.3 cm and a top rotor radius of 5.3 cm, at an RPM of 22,000 (38,000 g) the calculated time for a Dane particle core to be pelleted would be 110 minutes.

Sample Hydrolysis

The concentrated, reconstituted sample is treated with a base to hydrolyze the target nucleic acid and render it accessible. Nucleic acids are denatured and, if necessary, nicked by incubating the sample and collection device, if present, in 0.1 to 2.0 M base at 20 to 100° C. for 5 to 120 minutes. Preferably, treatment is achieved with 0.2 to 0.8 M NaOH, or a similar base such as KOH, at 60–70° C. for 30 to 60 minutes. Most preferably, the sample is incubated in 0.415 M NaOH at 65° C. for 45 minutes. Approximately one volume of sample is treated with one-half volume of base, also referred to herein as the hydrolysis reagent. The pH will be approximately 13. This basic pH will both nick and denature a majority of the nucleic acid in the specimen. In addition, base treatment disrupts interactions between peptides and nucleic acids to improve accessibility of the target nucleic acid, degrade protein, and liquify mucous. Base treatment of protein and mucous effectively homogenizes the specimen to ensure reproducibility of analysis results for a given sample. Base treatment also reduces the viscosity of the sample to increase kinetics, homogenize the sample, and reduce background by destroying any existing DNA-RNA or RNA-RNA hybrids in the sample. It is believed that base treatment also inactivates enzymes such as RNAases present in the sample that could potentially degrade RNA probes used in the assay.

Amplification

The nucleic acid sequences to be detected in the sample can be amplified in accordance with methods well known to those skilled in the art, prior to hydrolysis. Amplification is especially useful when the sample contains only trace amounts of the nucleic acid sequences to be detected. Methods of amplifying nucleic acid sequences are commercially available. Examples of applicable amplification systems that currently exist or are being developed include polymerase chain reaction (PCR), PCR in situ, ligase chain reaction (LCR), ligase hybridization, Qβ bacteriophage replicase, transcription-based amplification system (TAS), genomic amplification with transcript sequencing (GAWTS) and nucleic acid sequence-based amplification (NASBA). General reviews of these methods have been prepared by Landegren, U., et al., *Science* 242:229–237 (1988) and Lewis, R., *Genetic Engineering News* 10:1, 54–55 (1990). PCR technology is described in PCR Protocols A Guide to Methods and Applications by Michael A. Innis, David H. Gelfand, John J. Sninsky and Thomas J. White, pp. 39–45 and 337–385 (Academic Press, Inc., Harcourt Brace Jovanovich, Publishers, 1990). PCR technology is also described by Marx, J. L., *Science* 140:1408–1410 (1988) and in U.S. Pat. Nos. 4,683,195 and 4,683,202, to Mullis. Ligation amplification reaction is described by Wu, D. Y. and Wallace, R. B. *Genomics* 4:560–569 (1989) and Barringer, K. J., et al., *Gene* 89:117–122 (1990). Transcription based amplification reaction is described by Kwoh, D.Y., et al., *Proc. Natl. Acad. Sci. USA* 86:1173–1177 (1989).

These methods have the advantages of high sensitivity, but the disadvantages of being prone to false-positive results from reaction product contamination. For improved detection of amplified target nucleic acid sequences, a primer or primers, to which a ligand is attached, are used in accordance with the second preferred embodiment of the hybridization assay. The ligand is attached to the primer by conventional methods well known to those skilled in the art such as those described below for immobilization of anti-hybrid antibody to a solid phase. Alternatively, a commercially available ligand-bound primer is purchased from a supplier such as National Biosciences, Inc. (Plymouth, Minn.).

PCR using one primer is described by Loh, E. Y., et al., *Science* 243:217 (1989). This technique is often used with cDNA (DNA derived from messenger RNA by reverse transcriptase). There are also asymmetric PCR systems and other methods that use one primer or vast excess of one primer. These methods generate mostly single-stranded DNA, suitable for direct sequencing. Single primers can also be used with random hexamers (a degenerate mixture of all or most of the possible DNA hexamers) so that at least one hexamer will act as a second primer by hybridizing somewhere along the sequence at a distance from the first primer.

PCR in situ is the use of PCR amplification on cells or tissue sections followed by detection using in situ hybridization. This technique is described by Haase, A. T., et al., "Amplification and detection of lentiviral DNA inside cells", *Proc. Natl. Acad. Sci.* (USA) 87:4971–4975 (July 1990).

Ligase chain reaction is described by Wu, D. Y. and Wallace, R. B., *Genomics* 4:560–569 (1989) and Barringer, K. J., et al., *Gene* 89:117–122 (1990). Ligase hybridization is described by Landegren, U., et al., *Science* 241:1077–1080 (1988).

The Qβ bacteriophage replicase system is described by Kramer, F. R. and Lizardi, P. M., "Replicatable RNA reporters", *Nature* 339:401–402 (1989); Lizardi, P. M., et al., "Exponential amplification of recombinant-RNA hybridization probes", *Bio/Technology* 6:1197–1202 (1988); Lomeli, H., et al., "Quantitative assays based on the use of replicatable hybridization probes", *Clin. Chem.* 35:1826–1831 (1989); and Chu, B. C. F., et al., *Nucl. Acids Res.* 14:5591–5603 (1986). TAS is described by Kwoh, D. Y., et al., *Proc. Natl. Acad. Sci. USA* 86:1173–1177 (1989). GAWTS is described by Stoflet, E. S., et al., *Science* 239:491–494 (1988). NASBA is described by Compton, J., *Nature* 350:91–92 (1991).

Detection of Concentrated Nucleic Acids

The concentrated viral nucleic acids can be detected using any suitable process. Many methods of such detection are known and can be practiced routinely. The most preferred method for detection of nucleic acids is hybridization detection using specific hybridization probes. Grunstein et al., *Proc. Natl. Acad. Sci. USA* 72:3961 (1975) and Southern, *J. Mol. Biol.* 98:503 (1975) describe hybridization techniques using radiolabelled nucleic acid probes. Nucleic acid hybridization probes have the advantages of high sensitivity and specificity over other detection methods and do not require a viable organism. Hybridization probes are often labelled with a radioactive substance that can be easily detected.

The existing hybridization techniques that utilize radioisotopes to label probes introduce additional expenses for disposal of radioactive waste products and monitoring of personnel and the workplace for contamination. In addition, the short half-life of radioactive compounds such as $^{32}P$ requires that radioactive probes be produced frequently. Radioactive nucleic acid hybridization is therefore discouraged in commercial areas such as clinical diagnosis.

Probes have been indirectly labelled in an attempt to avoid the problems associated with direct radioactive labelling. The most common method of indirect labelling is to attach biotin, a small vitamin, to the nucleic acid using a chemical or enzymatic technique. Following hybridization, the biotin is detected by reaction with avidin, an egg white protein which has been labelled with an enzyme or fluorochrome. Bound enzyme can be detected by reaction with color-producing substrates and the fluorochrome can be seen when reacted with incident light of appropriate wavelength. Indirect labelling of hybridization probes with biotin or other haptens often increases the "hydrophobicity" of the probe. The probe tends to interact non-specifically with materials other than the complementary nucleic acid target, leading to high background. High background reduces sensitivity and increases the likelihood of a false-positive result. Indirect labelling is also less sensitive than direct labelling because the labelling density is limited; only a small fraction of the bases are labelled giving a limiting number of sites for signal generation. An increase in the labelling density of a probe leads to increased non-specific binding, higher background, and ultimately, failure of the probe to hybridize with its target due to the interference of the hapten with base pairing. Indirectly labelled probes are therefore not well suited to clinical diagnosis.

Probes can be prepared by methods known in the art. Preferably, the method uses non-radioactive RNA probes that can be synthesized or isolated in accordance with methods well known in the art as described by Maniatis, T., et al., *Molecular Cloning: A Laboratory Manual*, Cold Spring Harbor Laboratory, Cold Spring Harbor, N.Y. (1989). For example, HBV probes can be synthesized from linearized plasmid template using phage T7 RNA polymerase obtained from Life Technologies (Gaithersburg, Md.).

Preferably, the HBV RNA probes are a mixture of ad and ay subtypes. ad and ay subtypes are the most common subtypes found in clinical patients. The probes are preferably single-stranded RNA and approximately 3200 bases in length.

Preferably, the probe is diluted in a probe diluent that also acts as a neutralizing hybridization buffer. The diluent is used to dissolve and dilute the probe and also helps restore the sample to neutral pH, between approximately pH 6 and pH 9, to provide a more favorable environment for hybridization. Sufficient volume of probe diluent, preferably one-half volume, is used to neutralize one and one-half volume of base-treated sample. Preferably, the probe diluent is a 2-[bis(2-Hydroxyethyl) amino] ethane sulfonic acid (BES, Sigma, St. Louis, Mo.)/sodium acetate buffer. Most preferably, the probe diluent is a mixture of 2 M BES, 1 M sodium acetate, 0. 05% of the antimicrobial agent $NaN_3$, 5 mM of the metal chelating agent EDTA, 0.4% of the detergent Tween™-20 and 20% of the hybridization accelerator dextran sulfate. The pH of the probe diluent is between approximately 5 to 5.5. The concentration of each probe in the probe diluent is from 1 to 500 ng/ml. Preferably, the concentration of probe is 20 to 200 ng/ml. Most preferably, the concentration of each probe is approximately 75 ng/ml.

After treatment with base, an aliquot is removed from the sample tube and combined with a sufficient amount of probe, dissolved in the above-described probe diluent, to allow hybridization. Preferably, 150 μl of base-treated sample are neutralized with 50 μl probe diluent. The probes and sample nucleic acids are incubated for approximately 5 to 120 minutes at 20 to 80° C. to allow hybridization. Preferably, RNA probes and sample DNA are incubated for 30 to 60 minutes at 50 to 80° C. Most preferably, the RNA probes and DNA in the sample are incubated for 60 minutes at 65° C.

Hybridization has been detected with the use of an intercalating agent such as acridine orange or ethidium bromide as described in U.S. Pat. No. 4,563,417 to Albarella et al. The intercalating agent becomes inserted between hybridized base pairs of probe and sample nucleic acids and causes the tertiary structure of the helix to unwind. An antibody specific for the newly formed antigenic determinant created by the intercalating agent and the unwound helix is detected by conventional means. This method lacks selectivity for the target hybrids because intercalating agents fail to recognize specific sequences. Furthermore, the antibodies recognize only the intercalating agent/nucleic acid complex, but do not detect a specific sequence. Therefore, additional selection or purification steps are required to prevent non-specific signal, making this approach poorly suited for clinical diagnosis.

Preparation of Anti-hybrid Antibodies for Capture

Hybridization can be detected with the aid of an antibody specific for a labelled probe as described in U.S. Pat. No. 4,743,535 to Carrico. The probe is labelled with a detectable substance such as flavin adenine dinucleotide (FAD) or a fluorescent agent. An antibody specific for the labelled probe, after it has hybridized to the sample nucleic acid, is detected by a biochemical reaction. This method of detection also creates non-specific binding and the likelihood of false-positive results and is not well suited for clinical screening.

Monoclonal antibodies to DNA-RNA hybrids can also be used to detect hybridized probes. U.S. Pat. No. 4,732,847 to Stuart et al. and the publication of Stuart et al., *Proc. Natl. Acad. Sci., USA* 78:3751 (1981) describe a method of hybridization detection involving a monoclonal antibody specific for a poly(A)-poly(dT) duplex. A monoclonal antibody specific for DNA-RNA hybrids, secreted by hybridoma HB 8730, is disclosed in U.S. Pat. No. 4,833,084 to Carrico et al. The isolation of anti-DNA-RNA hybridomas has improved the development of assays for genetic mutations linked to specific defects and the detection of bacterial and viral infections. However, assays utilizing these anti-hybrid monoclonal antibodies often suffer from a high level of non-specific binding causing false positive results. Boguslawski et al., *J. Immunol. Methods* 89:123–130 (1986) developed a hybridization assay using anti-hybrid coated polystyrene beads isolated on filter paper in an attempt to reduce non-specific binding and avoid complicated washing procedures.

Any anti-hybrid antibodies may be used to capture the hybrid onto the solid phase that are specific for a double-stranded RNA/DNA. In a preferred embodiment of the present assay, a polyclonal anti-RNA/DNA hybrid antibody is derived from goats immunized with an RNA/DNA hybrid. Hybrid-specific antibody is purified from the goat serum by affinity purification against RNA/DNA hybrid immobilized on a solid support. Monoclonal antibody prepared using standard techniques can be used in place of the polyclonal antibodies.

The preferred antibody for capture of RNA/DNA hybrids is prepared by the method of Kitawaga, Y. and Stollar, B. D., *Mol. Immunology* 19:413–420 (1982) or according to the method set forth in U.S. Pat. No. 4,732,847 to Stuart et al. Both polyclonal and monoclonal anti-hybrid antibodies can be immobilized on the solid phase in the present assay as described below.

Immobilization of Anti-hybrid Antibody

The anti-hybrid antibody is immobilized onto a solid phase such as a test tube surface. It will be understood by those skilled in the art that a solid phase includes polystyrene, polyethylene, polypropylene, polycarbonate or any solid plastic material in the shape of test tubes, beads, microparticles, dip-sticks or the like. A solid phase also includes glass beads, glass test tubes and any other appropriate shape made of glass. A functionalized solid phase such as plastic or glass that has been modified so that the surface contains carboxyl, amino, hydrazide or aldehyde groups can also be used. Immobilization of the antibody can be direct or indirect. Preferably, test tubes are directly coated with anti-hybrid antibody in accordance with methods known to those skilled in the art or briefly described below. The antibody can also be biotinylated and subsequently immobilized on streptavidin coated tubes, or modified by other means to covalently bind to the solid phase. Solubilized biotinylated antibody can be immobilized on the streptavidin coated tubes before capture of the hybridized samples as described below or in conjunction with the addition of the hybridized samples to simultaneously immobilize the biotinylated antibody and capture the hybrids.

Most preferably, the antibody is attached to the solid phase in accordance with the method of Fleminger, G., et al., *Appl. Biochem. Biotech*. 23:123–137 (1990), by oxidizing the carbohydrate portion of the antibody with periodate to yield reactive aldehyde groups. The aldehyde groups are then reacted with a hydrazide-modified solid phase such as MicroBind-HZ™ microtiter plates available from Dynatech Laboratories (Chantilly, Va.). Passive coating of the antibody according to the well known method of Esser, P., Nunc Bulletin No. 6 (November 1988) (Nunc, Roskilde, Denmark) is also acceptable.

Alternatively, Ventrex Star™ tubes (Ventrex Laboratories Inc., Portland, Me.) are coated with streptavidin by the method of Haun, M. and Wasi, S., *Anal. Biochem.* 191:337–342 (1990). After binding of streptavidin the biotinylated goat polyclonal antibody described above, or otherwise produced by methods known to those skilled in the art, is bound to the immobilized streptavidin. Following antibody binding, tubes can be post-coated with a detergent such as Tween™-20 and sucrose to block unbound sites on the tube and stabilize the bound proteins as described by Esser, P., Nunc Bulletin No. 8, pp. 1–5 (December 1990) and Nunc Bulletin No. 9, pp. 1–4 (June 1991) (Nunc, Roskilde, Denmark) and Ansari, et al., *J. Immunol. Methods* 84:117–124 (1985). Preferably, each tube is coated with between 10 ng and 100 μg biotinylated antibody. Most preferably each tube is coated with approximately 250 ng of biotinylated antibody.

As discussed above, the solid phase can be coated with functional antibody fragments or derivatized functional fragments of the anti-hybrid antibody.

Capture

Hybridized samples are incubated in the anti-hybrid coated tubes for a sufficient amount of time to allow capture of the hybrids by the immobilized antibodies. The hybrids are bound to the immobilized antibodies by incubation for 5 minutes to 24 hours at 15 to 65° C. on a platform shaker with a shaking speed of 0 to 1500 rpm. Preferably, the incubation time is 30 to 120 minutes at 20 to 40° C., with shaking at 300 to 1200 rpm. Most preferably, capture occurs with incubation at one hour at room temperature with vigorous shaking on a rotary platform shaker with a rotary shaking speed between approximately 300 and 1000 rpm. It will be understood by those skilled in the art that the incubation time, temperature, and shaking can be varied to achieve alternative capture kinetics as desired.

Conjugation of Anti-hybrid Antibody

An antibody, specific for the RNA/DNA hybrid is conjugated to a label for detection of captured hybridized probe by well known conjugation methods. Preferably, an antibody, such as the mouse monoclonal antibody deposited with the American Type Culture Collection as ATCC Accession number HB-8730, is conjugated to a detectable label such as alkaline phosphatase. It will be understood by those skilled in the art that any detectable label such as an enzyme, a fluorescent molecule or a biotin-avidin conjugate can be used.

The antibody conjugate is produced by well known means such as direct reduction of the monoclonal antibody with dithiothreitol, (DTT, Sigma Chemical Company, St. Louis, Mo.) to yield monovalent antibody fragments. The reduced antibody is then directly conjugated to maleimated alkaline phosphatase by the methods of Ishikawa et al., *J. Immunoassay* 4:209–237 (1983) and Means, G. and Feeney, R., *Bioconj. Chem.* 1: 2–12 (1990) and the resulting conjugate is purified by HPLC.

Alternatively, captured hybrid can be detected indirectly using an unlabelled anti-hybrid antibody for which a labelled antibody is specific. For example, the anti-hybrid antibody can be a mouse immunoglobulin that is detected by a labelled goat anti-mouse antibody.

In addition, captured hybrid can be detected by conjugating the RNA probe used for hybridization to a label, such as an enzyme, or to a hapten, such as biotin that is then detected with a labelled anti-hapten antibody.

Excess Probe Digestion and Hybrid Detection

After capture, any excess sample is removed from the capture tube, a solution preferably containing both a single-stranded RNA digestion enzyme such as RNAase at a concentration between 0.01 and 1 mg/ml and the above described conjugated anti-hybrid molecule is added to the tube, and the tube is incubated for approximately 5 minutes to 24 hours at temperature between 4 and 45° C. The purpose of the RNA digestion enzyme is to degrade non-hybridized probe that may be bound to the tube. It is important to remove the excess probe because secondary structures in the nucleic acid can be recognized by the detection means, resulting in elevated assay background. Preferably, the enzyme is added at a concentration between 0.05 and 0.5 mg/ml and is incubated for between 10 and 60 minutes. Most preferably, the enzyme is RNase A (Sigma, St. Louis, Mo.) and is incubated with the captured DNA for approximately 30 minutes at a concentration of 200 μg/ml. RNase III (NCI, Frederick, Md.) can also be used.

The RNase and conjugate are preferably diluted in a conjugation buffer that promotes specific antibody-antigen interaction, blocks non-specific binding of conjugate to the capture tube and stabilizes conjugate for long-term storage. A preferred buffer contains 0.1 M TrisTM ™-HCl, pH 7.5, 0.6 M NaCl to reduce cross reaction of antibody with other nucleic acid species, $ZnCl_2$ and $MgCl_2$ for stabilizing alkaline phosphatase, normal goat serum to block non-specific interaction of conjugate with the capture surface, 0.25% Tween™-20 to block non-specific binding of conjugate, and sodium azide as a preservative. A preferred wash buffer contains 0.1 M Tris™-HCl, pH 7.5, 0.6 M NaCl, 0.25% Tween™-20, and sodium azide as a preservative.

Detection of captured hybrid is preferably achieved by binding the above-described conjugated anti-hybrid molecule to the hybrid during this incubation. Tubes are then washed with the above-described wash buffer to remove any excess conjugate. Preferably, five manual washes are performed using either an Eppendorf Repeat Pipettor with a 50 ml Combitip™ (Eppendorf, Hamburg, Germany), a Corning™ repeat syringe (Corning, Corning, N.Y.), a simple pump regulated by a variostat, or by gravity flow from a reservoir with attached tubing. Commercially available tube washing systems available from Source Scientific Systems (Garden Grove, Calif.) can also be used.

As described above, captured hybrid can also be detected with a direct labelled RNA probe, such as an enzyme-conjugated hybridization probe, or a hapten-modified probe that is subsequently detected by a labelled anti-hapten antibody.

Bound conjugate is subsequently detected by colorimetry or chemiluminescence as described by Coutlee, et al., *J. Clin. Microbiol.* 27:1002–1007 (1989). Preferably, bound alkaline phosphatase conjugate is detected by chemiluminescence with a reagent such as a Lumi-Phos™ 530 reagent (Lumigen, Detroit, Mich.) using a detector such as an E/Lumina™ luminometer (Source Scientific Systems, Inc., Garden Grove, Calif.) or an Optocomp I™ Luminometer (MGM Instruments, Hamden, Conn.).

The following non-limiting examples illustrate use of the disclosed assay.

EXAMPLE 1

In this experiment two different serum samples known to be positive for Hepatitis B DNA by HCM II assay were used. One sample was a low positive at 1.57 pg/ml or $4.4 \times 10^5$ genomes/ml, referred to as PC low, and the other one PC high at 209 pg/ml or $5.85 \times 10^7$ genomes/ml. In this experiment after the centrifugation (both 1 ml and 0.5 ml samples were used) the pellets were reconstituted in 30 μl of HBV DNA negative human serum. The pelleting for each sample was performed in triplicate and results compared to the standard protocol without the centrifugation.

HBV DNA in serum samples was quantitated by a non-radioactive hybridization assay by pipetting 30 μl control or sample serum into microplate wells. A 30 μl aliquot of a hydrolyzing reagent was pipetted into each well. A 30 μl aliquot of HBV probe was pipetted into each well. The plate was mixed and incubated at 65° C. for 60±5 minutes. The contents of each well was transferred to a microplate well coated with anti-hybrid antibody. The microplate was covered with Parafilm™ and shaken on a rotary shaker for 60 minutes. The plate was decanted and blotted. A 75 μl aliquot of detection reagent containing RNAase A and an alkaline phosphatase-conjugated monoclonal antibody specific for the RNA/DNA hybrid was pipetted into each well, the plate was incubated at room temperature for 30±3 minutes, decanted, washed six times and drained. A 75 μl aliquot of a second detection reagent containing a chemiluminescent alkaline phosphate substrate was pipetted into each tube and incubated at room temperature for 15±3 minutes. The plate wells were read on a luminometer.

The results, obtained in triplicate for both the standard and the 1 ml and 0.5 ml centrifuged test volumes are shown in Table 2. Coefficient of Variations are calculated for the triplicate samples. Results are expressed in Relative light units and the concentrations are in genomes/ml derived from a standard curve.

TABLE 2

|  | Standard genomes/ml | 1 ml centrifuged genomes/ml | 0.5 ml centrifuged genomes/ ml |
|---|---|---|---|
| PC low | $4.4 \times 10^5$ genomes/ml | $1.1 \times 10^7$ genomes/ml | $7.0 \times 10^6$ genomes/ml |
| PC high | $5.8 \times 10^7$ genomes/ml | $1.58 \times 10^9$ genomes/ml | $1.1 \times 10^9$ genomes/ml |

For the 1 ml pre-centrifugation volume sample, the expected increase in concentration is 33.3 times (1000 μl/30 μl) and with the 0.5 ml sample the expected increase is 16.6 times. The actual increases for the 1 ml sample were 25 times for the PC low and 27 times for the PC high. The 0.5 ml sample showed an increase of 16 times and 19 times, respectively. The recovery was about 75%.

EXAMPLE 2

The scheme was slightly changed in this experiment. To further evaluate the increased sensitivity in the functional testing of the concentrated material serial four-fold dilutions were prepared from the virion containing sample referred to as PC low, prior to the centrifugation. The dilutions were prepared in a negative serum at 1:4, 1:16, 1:64, 1:256 and 1:1024. Dilutions of the material (either 1 ml or 0.5 ml) were centrifuged for concentration. In this experiment after the centrifugation the pellets were reconstituted in 20 μl of negative serum and volumes re-measured with a pipet to make sure the pellet got reconstituted in a total volume of 30 μl. The pelleting for each sample was performed in triplicate and results compared to the standard protocol (SOP) without the centrifugation.

The data are summarized below in Table 3

TABLE 3

|  | SOP | | 1 ml concentrated | | | 500 μl concentrated | | |
|---|---|---|---|---|---|---|---|---|
|  | Expected | Observed genomes/ml | Exp | Observed genomes/ml | O/E | Exp | Observed genomes/ml | O/E |
| PC low undil | 445,184 | 445,184 | $1.47 \times 10^7$ | $1.57 \times 10^7$ | 1.1 | $7.39 \times 10^6$ | $8.04 \times 10^6$ | 1.08 |
| 1:4 | 111,296 | 120,400 | $3.67 \times 10^6$ | $3.72 \times 10^6$ | 1 | $1.84 \times 10^6$ | $1.66 \times 10^6$ | 0.9 |
| 1:16 | 27,824 | neg | $9.16 \times 10^5$ | $7.95 \times 10^5$ | 0.9 | $4.59 \times 10^5$ | $3.98 \times 10^5$ | 0.86 |
| 1:64 | 6956 | neg | $2.29 \times 10^5$ | $1.93 \times 10^5$ | 0.9 | $1.15 \times 10^5$ | $1.12 \times 10^5$ | 0.97 |
| 1:256 | 1739 | neg | $5.77 \times 10^4$ | $7.56 \times 10^4$ | 1.35 | $2.86 \times 10^4$ | $6.44 \times 10^4$ | NA |
| 1:1024 | 434 | neg | $1.39 \times 10^4$ | neg | NA | $7.14 \times 10^3$ | Neg | NA |

The advantage of concentrating a low positive serum sample can be clearly observed. In the standard operating procedure sample, using the standard volume of test (30 μl) and no centrifugation the PC low sample can only be detected undiluted. The SOP assay detection limit is 0.5 pg/ml or $1.4 \times 10^5$ genomes/ml. When 1 ml is concentrated with the centrifugation procedure, up to the 1:64 dilution (0.69 pg/ml or 6870 genomes/ml) can be detected. The percent recovery is between 86 to 100%. The 1 ml concentration volume is positive to a level of 6956 genomes/ml, an increase in the assay detection limit of 20×. This 20-fold increase is derived from the minimum genome/ml concentration of 6956 divided into 140,000, the assay sensitivity in the SOP. The 500 μl concentrated sample is positive to below the 1:16 dilution, equivalent to 27,500 genomes/ml.

By increasing the volume of sample to test to 1 ml and performing the centrifugation step described in detail above, the sensitivity in the detection of Hepatitis B DNA in serum with can be increased by approximately 20-fold, down to about 6956 genomes/ml.

Publications cited herein and the material for which they are cited are specifically incorporated by reference.

Those skilled in the art will recognize, or be able to ascertain using no more than routine experimentation, many equivalents to the specific embodiments of the viral detection method described herein. Such equivalents are intended to be encompassed by the following claims.

We claim:

1. An assay for the detection of hepatitis B DNA in a biological sample, the method comprising
concentrating a hepatitis B viral particle comprising the target nucleic acid sequence by centrifugation of the biological sample, wherein the biological sample is centrifuged for a length of time determined by the following equation:

$$T = \frac{1}{s} \frac{(\ln r_i - \ln r_o)}{(0.1047 \cdot \text{RPM})^2}$$

where s is $110 \times 10^{-13}$ seconds, $r_t$ is the rotor bottom radius, $r_o$ is the rotor top radius, RPM is the revolutions per minute of the rotor, and T is the time in seconds, wherein the hepatitis B particle is pelleted, resuspending the pelleted hepatitis B viral particle in human serum negative for hepatitis B DNA, and detecting the concentrated hepatitis B DNA.

2. The assay of claim 1, wherein the biological sample is combined with a precipitation buffer prior to centrifutigation.

3. The assay of claim 1 wherein RPM is above 15,000.

4. The assay of claim 3 wherein RPM is above 20,000.

5. The assay of claim 1, wherein detection is accomplished by
   a) treating the sample with a base;
   b) hybridizing a nucleic acid sequence in the treated sample to a complementary nucleic acid probe to form a double-stranded hybrid;
   c) capturing the hybrid onto a solid phase to which an anti-hybrid antibody or anti-hybrid fragment has been immobilized;
   d) eliminating any non-hybridized probe; and
   e) detecting the bound hybrid.

6. The assay of claim 5, wherein the biological sample is serum obtained by separation of the serum from a blood sample.

7. The assay of claim 5 wherein the non-hybridized probe is eliminated by digestion with an enzyme.

8. The assay of claim 5 wherein the probe is an RNA sequence complementary to target nucleic acid sequence.

9. A hybridization assay for the detection of hepatitis B DNA in blood comprising the steps of:
   a) separating serum from the blood;
   b) concentrating hepatitis B viral particles comprising hepatitis B DNA by combining the serum with a precipitation buffer and then centrifuging the combined serum and buffer for a length of time sufficient to pellet the hepatitis B viral particles as determined by the following equation:

$$T = \frac{1}{s} \frac{(\ln r_i - \ln r_o)}{(0.1047 \cdot \text{RPM})^2},$$

where s is $110 \times 10^{-13}$ seconds, $r_t$ is the rotor bottom radius, $r_o$ is the rotor top radius, RPM is the revolutions per minute of the rotor, and T is the time in seconds;

c) resuspending the pelleted hepatitis B viral particles in human serum negative for hepatitis B DNA:
   d) treating the sample with a base to denature the hepatitis B DNA;
   e) hybridizing the denatured hepatitis B DNA in the treated sample to a complementary nucleic acid probe to form a double-stranded hybrid;
   f) capturing the hybrid onto a solid phase to which an anti-hybrid antibody or anti-hybrid fragment has been immobilized;
   g) eliminating any non-hybridized probe; and
   h) detecting the bound hybrid.

10. The assay of claim 9 wherein RPM is above 15,000.

11. The assay of claim 10 wherein RPM is above 20,000.

12. An assay for the detection of hepatitis B nucleic acid sequence in a biological sample, the method comprising concentrating a hepatitis B particle comprising the hepatitis B nucleic acid sequence by centrifugation of the biological sample, wherein the biological sample is combined with a precipitation buffer and then centrifuged for a length of time determined by the following equation:

$$T = \frac{1}{s} \frac{(\ln r_i - \ln r_o)}{(0.1047 \cdot \text{RPM})^2},$$

where s is the sedimentation coefficient of the hepatitis B particle, $r_t$ is the rotor bottom radius, $r_o$ is the rotor top radius, RPM is the revolutions per minute of the rotor, and T is the time in seconds, wherein the hepatitis B particle is pelleted, resuspending the pelleted hepatitis B particle in serum negative for hepatitis B DNA, and detecting the concentrated hepatitis B DNA.

* * * * *